United States Patent [19]
Reisinger

[11] Patent Number: 5,496,329
[45] Date of Patent: Mar. 5, 1996

[54] METHOD AND APPARATUS FOR IMPLANTING A MEDICAL VENTILATION TUBE

[75] Inventor: John R. Reisinger, Saint Cloud, Minn.

[73] Assignee: Alpha Surgical, Inc., Eau Claire, Wis.

[21] Appl. No.: 118,500

[22] Filed: Sep. 8, 1993

[51] Int. Cl.$^6$ .................................................. A61B 17/00
[52] U.S. Cl. .......................... 606/109; 606/108; 604/264; 128/898
[58] Field of Search ............................. 606/1, 108, 109; 128/898; 604/264

[56] References Cited

U.S. PATENT DOCUMENTS

| | | | |
|---|---|---|---|
| D. 276,937 | 12/1984 | Griggs | D24/34 |
| 3,530,860 | 9/1970 | Majoros. | |
| 3,645,268 | 2/1972 | Capote. | |
| 3,807,409 | 4/1974 | Paparella et al.. | |
| 3,871,380 | 3/1975 | Heros. | |
| 3,888,258 | 6/1975 | Akiyama. | |
| 3,897,786 | 8/1975 | Garnett et al.. | |
| 3,913,584 | 10/1975 | Walchle et al.. | |
| 3,948,271 | 4/1976 | Akiyama. | |
| 4,094,303 | 6/1978 | Johnston | 128/1 R |
| 4,168,697 | 9/1979 | Cantekin | 128/1 R |
| 4,174,716 | 11/1979 | Treace. | |
| 4,191,191 | 3/1980 | Auburn. | |
| 4,326,512 | 4/1982 | Peerless | 128/151 |
| 4,468,218 | 8/1984 | Armstrong | 604/49 |
| 4,473,073 | 9/1984 | Darnell. | |
| 4,695,275 | 9/1987 | Bruce et al. | 604/264 |
| 4,704,126 | 11/1987 | Baswell et al. | 623/10 |
| 4,733,671 | 3/1988 | Mehl | 128/754 |
| 4,744,792 | 5/1988 | Sander et al. | 623/10 |
| 4,808,171 | 2/1989 | Berger | 604/264 |
| 4,913,132 | 4/1990 | Gabriel | 128/9 |
| 4,971,076 | 11/1990 | Densert et al. | 128/898 |
| 5,026,378 | 6/1991 | Goldsmith | 606/109 |
| 5,147,376 | 9/1992 | Pianetti | 606/170 |
| 5,178,623 | 1/1993 | Cinberg et al. | 606/109 |
| 5,207,685 | 5/1993 | Cinberg et al. | 606/109 |
| 5,236,455 | 8/1993 | Wilk et al. | 623/10 |
| 5,254,120 | 10/1993 | Cinberg et al. | 606/109 |

OTHER PUBLICATIONS

Microtek Medical, Microtek Ventilation Tubes Catalog Publication date unknown.
OTO–MED, Inc., Micro–Surgery Products/Otorhinolaryngology Catalog Publication date unknown.
Storz, Surgical Instruments Catalog Publication date unknown.
Smith & Nephew/Richards, Buyer's Guide for Ventilation Tubes Publication date unknown.
Smith & Nephew/Richards, 1990–91 Microsurgery Catalog Publication date unknown.
Smith & Nephew/Richards, Disposable Instruments Catalog Publication date unknown.

*Primary Examiner*—Stephen C. Pellegrino
*Assistant Examiner*—Glenn Dawson
*Attorney, Agent, or Firm*—Briggs and Morgan

[57] ABSTRACT

The preferred embodiment of the apparatus comprises the combination of a fixture and ventilation tube, with the fixture including a mandrel that is engagingly received through the bore or lumen of the ventilation tube to define a distal tip projecting from the front face of the ventilation tube. A helical thread extends rearwardly from the distal tip of the fixture to the seating region of the ventilation tube along a conical surface formed by portions of both the fixture and ventilation tube.

The preferred method of this invention for implanting a ventilation tube through the membrane includes the steps of: providing a fixture and ventilation tube with a helical thread and penetrating edge, placing that penetrating edge in contact with the membrane rotating the penetrating edge so that it penetrates the membrane to simultaneously form a passage and draw the ventilation tube into that passage at a controlled rate until the ventilation tube is implanted, and detaching the fixture from the ventilation tube so that the ventilation tube remains implanted through the membrane at the desired location.

30 Claims, 5 Drawing Sheets

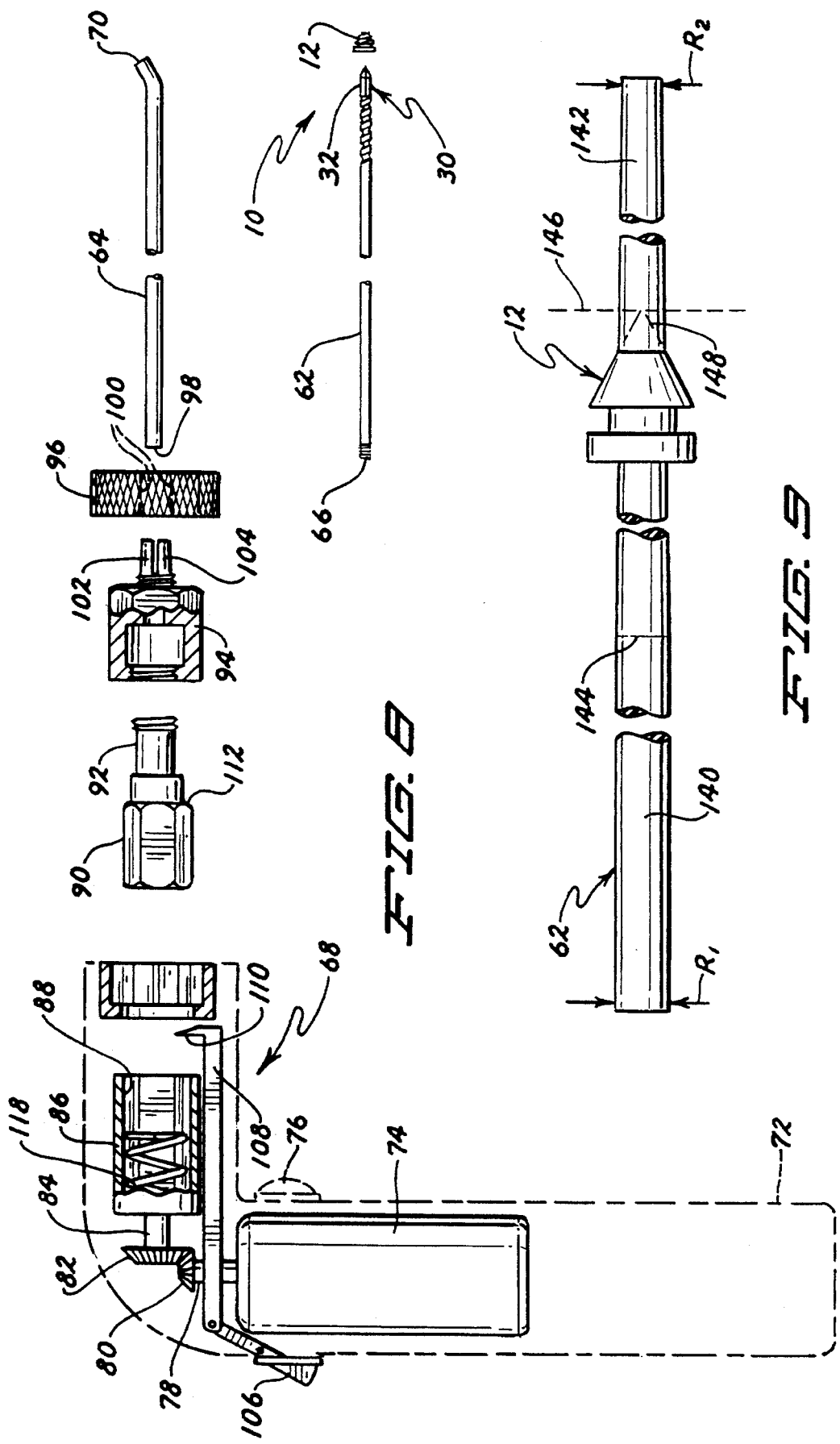

METHOD AND APPARATUS FOR IMPLANTING A MEDICAL VENTILATION TUBE

BACKGROUND OF THE INVENTION

1. Field of the Invention

This invention relates generally to devices for implanting a medical ventilation tube through a thin membrane of a person, and particularly to a method and apparatus for implanting an otological ventilation tube through the tympanic membrane in which the rotation of the ventilation tube simultaneously creates a passage penetrating the substantially intact membrane and draws the ventilation tube through that passage.

2. Prior Art

Ventilation tubes are frequently implanted in or through the tympanic membrane to treat middle ear effusions by permitting ventilation, draining fluid discharge from the middle ear and allowing pressure equalization between the middle and outer ear. Various types of ear ventilation tubes, grommets, and similar prostheses are employed in such medical procedures and are manufactured in a wide variety of styles and designs particularly suited or adapted for specific purposes.

Conventionally, a ventilation tube was implanted by making a linear incision in the lower anterior quadrant of the tympanic membrane, draining excess fluid which had accumulated in the middle ear, and then inserting the leading end of the ventilation tube through the incision. Because the body of the ventilation tube is usually cylindrical and the incision is straight, and further because the leading end of the ventilation tube frequently incorporates an enlarged flange or projection, the incision occasionally permits premature extrusion or dislocation of the ventilation tube.

Incisions that were too large or too small would result in dislodged ventilation tubes, tearing of the tympanic membrane, or incisions that would not heal properly, thus requiring subsequent surgical repair or reconstruction. Since the ventilation tube was placed through the incision using forceps, obtaining the proper positioning and orientation of the ventilation tube within a restricted ear canal could be difficult. In some cases, the ventilation tube could be accidentally pushed entirely into the middle ear and released, requiring a surgical procedure for removal.

More recently, methods for implanting ventilation tubes have been developed which are designed to reduce or eliminate the initial incision. Modified ventilation tubes have been specifically developed to work in cooperation with these methods of implantation.

One representative example is U.S. Pat. No. 3,807,409 to Paparella, which discloses a medical ventilation tube having a notched inner or leading flange which permits one tapered edge to be inserted through an initial incision in the tympanic membrane, and then by rotating the body of the ventilation tube until the entire leading flange traverses from the outer side to the inner side of the membrane. This procedure permits an incision that is smaller than the maximum diameter of the inner flange without intentionally stretching the tympanic membrane, although the incision must still be larger than the body of the ventilation tube between the inner and outer flanges. Paparella '409 also discloses a rearwardly projecting flexible tab designed to facilitate the use of forceps in a nearly closed position, thus permitting increased access in a restricted ear canal, but decreasing the accuracy and precision with which the ventilation tube can be positioned or oriented.

U.S. Pat. No. 5,026,378 to Goldsmith discloses a method for implanting a ventilation tube in which the ventilation tube is mounted on a trocar that extends through the central bore or lumen of the ventilation tube and has a pointed distal tip. The distal tip is used to puncture the tympanic membrane by direct pressure exerted from the trocar on the membrane, and the truncated conical leading flange of the resilient ventilation tube is then forced through the aperture created by the distal tip of the trocar. The rear face of the ventilation tube abuts a sleeve which circumscribes the trocar and is attached to the myringotomy instrument. Manually retracting the trocar through the ventilation tube and sheath detaches the ventilation tube from the trocar and instrument. Goldsmith '378 further discloses providing the distal tip of the trocar with blades that extend directly rearward from the pointed tip to approximately one third the length of the conical region, and which assist in puncturing the membrane along predetermined lines to minimize the extent to which the membrane will tear along jagged edges or produce a non-uniform incision.

While Goldsmith '378 discloses a truncated conical leading flange that is generally coplanar with the outer surface of the conical distal tip (with the two surfaces being sufficiently proximate to one another so as to practically form continuations of one another), one important drawback of Goldsmith '378 is that the leading flange of the ventilation tube is substantially greater in diameter than the diameter of the trocar, thus increasing the likelihood that the membrane will tear jaggedly or produce a non-uniform incision that may not heal properly.

Significant pressure must be exerted directly on the tympanic membrane in order to stretch the incision sufficiently to insert the leading flange of the ventilation tube. This increased axial pressure can distort the tympanic membrane to the point where the membrane or trocar are dangerously close to or actually contact the delicate structures of the middle or rarely the inner ear, which are sometimes disposed as little as 2 mm from the normal plane of the membrane.

Another significant disadvantage of the Goldsmith '378 apparatus is that the distal tip of the trocar can slide along the tympanic membrane or become displaced from the most advantageous location for the ventilation tube as pressure is exerted on the trocar to puncture the membrane, particularly in the lower quadrant of the membrane where the angle between the membrane and the ear canal diverge the farthest. Consequently, ventilation tubes must frequently be implanted in less desirable or suitable quadrants of the tympanic membrane when using the Goldsmith '378 method, so that the trocar may be maintained as perpendicular as possible to the plane of the membrane without excess slippage.

Other representative examples in which a trocar or needle on which the ventilation tube is mounted is used to initially pierce the membrane are shown in U.S. Pat. Nos. 3,913,584 to Walchle; 3,530,860 to Majoros; and 3,888,258 and 3,948,271 to Akiyama. In addition, U.S. Pat. No. 3,645,268 to Capote discloses a ventilation tube having an open spearhead-shaped tip for piercing the membrane which remains connected to the ventilation tube within the middle ear subsequent to implantation of the ventilation tube.

BRIEF SUMMARY OF THE INVENTION

It is therefore one object of this invention to develop a method and apparatus for rapidly implanting a ventilation tube through a tympanic or similar membrane at a desired location without making an initial incision or requiring perpendicular force being applied to puncture the membrane, and further such that the resulting passage is the optimal minimum size for seating the ventilation tube to reduce the risk of premature extrusion from the passage.

It is another object of this invention to design the method and apparatus such that the ventilation tube will penetrate through the membrane at a rate which may be precisely controlled, and so that the rate of penetration and the linear progression of the of the ventilation tube through the membrane may be monitored and selectively controlled by the physician without reference to any external scale or reference.

It is a related object of this invention to design the method and apparatus such that the ventilation tube may be installed in the most desirable location of the membrane, without regard to the angle formed between the plane of the membrane and the distal tip of the instrument or the relative constriction of any surrounding passageway through which the membrane can be accessed.

It is yet another object of this invention to design the above method and apparatus so as to minimize the potential for damaging or tearing the membrane itself, as well as the potential for distorting the membrane from its normal plane to the point at which the membrane or instrument contact and damage other delicate structures located on the opposite side of the membrane.

In particular, it is a related object of this invention to design the above method and apparatus so as to permit use of the ventilation tube and implantation instrument to retract or pull the membrane away from any physiological structures disposed on the opposite side of the membrane, thereby allowing additional clearance to perform the implantation procedure.

It is a distinct object of this invention to design the above method and apparatus such that the implantation procedure may be accomplished by a physician using one hand, without the subsequent use of ancillary surgical instruments to complete the implantation.

It is a further object of this invention to design the above method and apparatus such that the portion of the instrument exposed to contact with the patient is disposable, and may be supplied in a sterile package with one of a wide variety of ventilation tubes mounted for immediate implantation using standardized equipment, and may be adapted for use with many existing types of ventilation tubes.

Briefly described, the apparatus of this invention comprise: a fixture and ventilation tube mounted thereon having a helical thread extending longitudinally rearward from the distal tip of the fixture to the outer peripheral edge of the forward or leading flange of the ventilation tube along a substantially continuous and coplanar conical surface formed by portions of both the fixture and ventilation tube. The fixture may include a mandrel which is engagingly received through the bore or lumen of the ventilation tube and defines the distal tip of the apparatus, and which is retracted from the bore once the ventilation tube has been at least partially implanted through the membrane.

The method of this invention for implanting a ventilation tube through a thin membrane comprises the steps of (1) providing a fixture and ventilation tube with a helical thread or penetrating edge, (2) placing that penetrating edge in contact with the membrane at the desired location where the ventilation tube is to be implanted, (3) rotating the penetrating edge at a selectively controllable angular speed so that it penetrates the membrane to simultaneously form a passage and draw the ventilation tube into that passage at a controlled rate until the linear advancement of the ventilation tube is arrested by the termination of the helical thread and the ventilation tube's rear flange, and (4) detaching the fixture from the ventilation tube so that the ventilation tube remains implanted through the membrane at the desired location.

BRIEF DESCRIPTION OF THE DRAWINGS

FIG. 8 is a diagrammatic view of the hand-held embodiment of the instrument used to implant ventilation tubes according to the method and apparatus of this invention, including the rotational drive assembly, the retraction mechanism, and the disposable elements;

FIG. 9 is an detailed view of an embodiment in which the ventilation tube is initially mounted on the tapered end segment of a solid shaft.

DESCRIPTION OF THE PREFERRED EMBODIMENTS

The method and apparatus for implanting a ventilation tube of this invention are shown in FIGS. 1–10 and referenced generally therein by the numeral 10.

Figure 2:
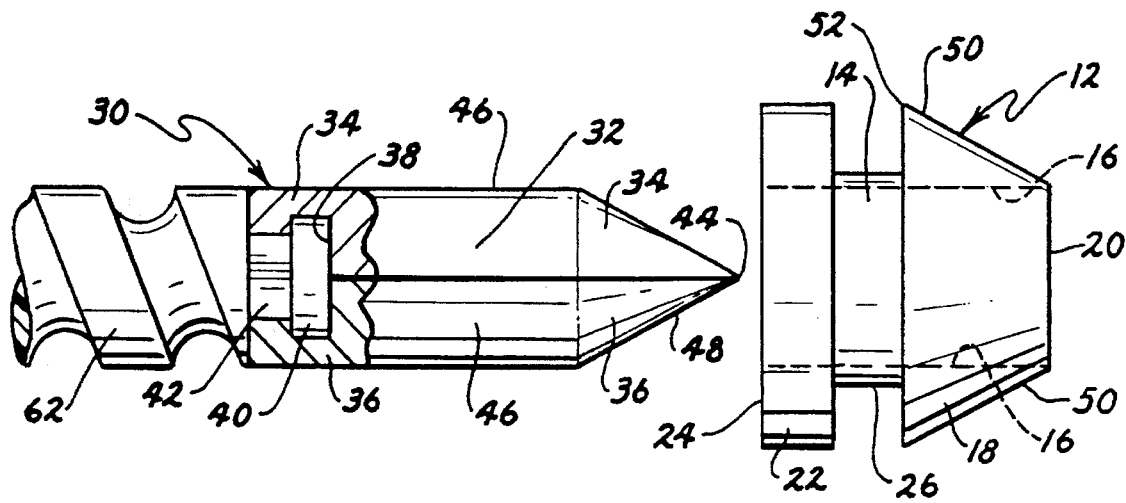
FIG. 2 a side elevation view of the mandrel embodiment of the fixture and the corresponding ventilation tube of this invention with the mandrel disposed apart from the ventilation tube.

Referring particularly to FIG. 2, a ventilation tube 12 is shown that is similar to a tab-less Shea parasol ventilation tube having a body 14 defining a central lumen or bore 16, a forward section or flange 18 having a front face 20, and a rear section or flange 22 having a rear face 24. Each of the forward flange 18 and rear flange 22 have diameters substantially greater than the outer diameter of the body 14, to define a generally cylindrical seating region 26 around which the membrane 28 rests with the forward flange 18 and rear flange 22 disposed on opposing sides of the membrane 28 to restrain axial movement of the ventilation tube 12 within a predetermined range.

Conventional ventilation tubes 12 and related prostheses are preferably constructed from rigid lightweight metals or resilient polymers, the most frequently used materials being gold, silver, titanium, tantalum, platinum, stainless steel, fluroplastics, hydroxylapatite, silicone, polyethylene, Teflon®, and Dacron® used individually or in various combinations. The ventilation tube of this invention may be fabricated from any of these materials according to the particular characteristics and requirements of the ventilation tube. However, for the particular embodiment of the ventilation tube described herein, titanium of the type employed in conventional otological ventilation tubes has proven suitable.

Referring again to FIG. 2, a fixture 30 is shown to which the ventilation tube 12 is mounted or engagingly attached to accomplish the implantation procedure. In the embodiment shown in FIGS. 2–5, the fixture 30 is or includes a mandrel 32 which is divided longitudinally into two or more mating sections 34, 36 and together define an interior recess 38 that at least partially encloses and engages a head 40 which extends from the end of a base member 42 to prevent or restrict axial movement and rotation of the mating sections 34, 36 of the mandrel 32 relative to the base, member 42. The mandrel 32 has a distal end 44 and a generally uniform cylindrical outer surface 46.

Figure 3:
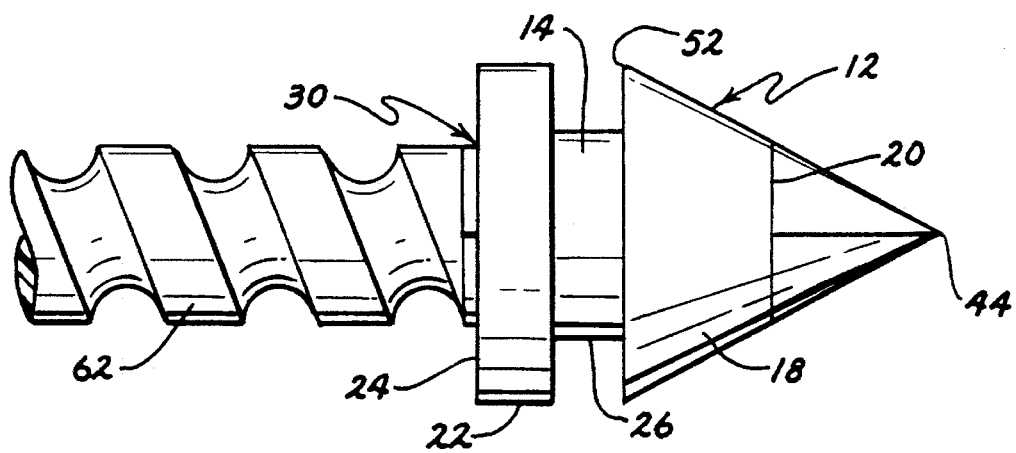
FIG. 3 is a side elevation view of the mandrel and ventilation tube of FIG. 2 showing the mandrel received within the ventilation tube such that the distal end protrudes beyond the front face of the ventilation tube.
Figure 4:
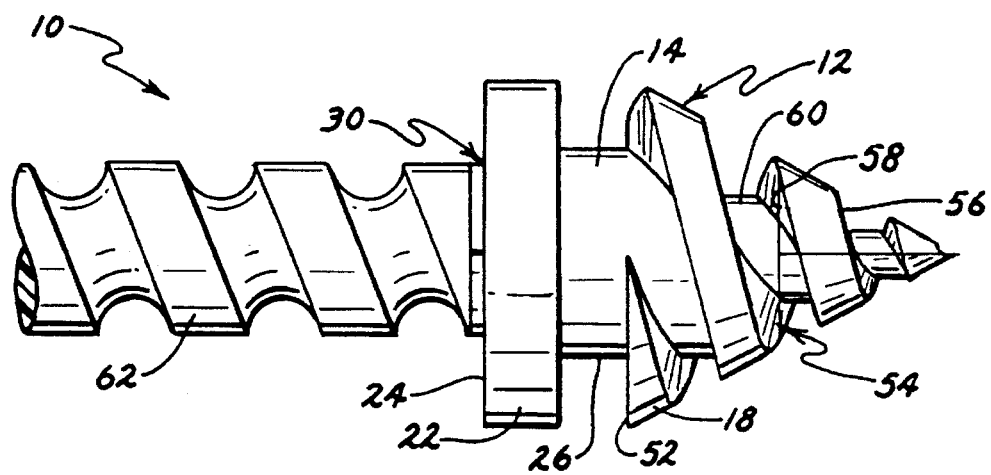
FIG. 4 is a side elevation view of the mandrel and ventilation tube of FIG. 2 showing the helical thread formed along and into the adjoining conical surfaces of the distal end of the mandrel and front section of the ventilation tube.

Referring to FIGS. 2–4, the mandrel 32 is inserted through the bore 16 of the ventilation tube 12 until the distal end 44 extends beyond the front face 20 of the ventilation tube 12. The inner diameter of the bore 16 of the ventilation tube 12 is slightly undersized compared with the outer diameter of the cylindrical outer surface 46 of the mandrel 32 so that the position and orientation of the ventilation tube are maintained relatively constant due to the friction or pressure fit between the inner surface of the bore 16 and the outer surface 46 of the mandrel 32. As a representative example, a stainless steel ventilation tube 12 having an overall length of 2 mm and an outer diameter of 2.5 mm at the forward flange 18 would utilize a differential of 0.02 mm between the inner diameter of the bore 16 and the outer diameter of the cylindrical outer surface 46 of the mandrel 32.

The distal end 44 of the mandrel 32 may include a beveled or conical segment 48 having the same angle relative to the longitudinal axis of the mandrel 32 as the truncated conical segment 50 of the forward flange 18 of the ventilation tube 12 between the junction of the front face 20 and the bore 16 and the outer radial surface 52 of the forward flange 18, such that the beveled segment 48 and truncated conical segment 50 are aligned with and proximate to one another to form a substantially continuous and coplanar conical surface having a uniform angle relative to the longitudinal axes of the bore 16 and mandrel 32.

Alternately, the distal end 44 of the mandrel 32 and the forward flange 18 of the ventilation tube 12 may be enlarged or irregular in shape, and once the ventilation tube 12 is mounted on the mandrel 32 with a portion of the distal end 44 extending beyond the front face 20 of the ventilation tube 12 the distal end 44 of the mandrel 32 and the segment 50 of the forward flange 18 are simultaneous cut, ground, and polished to form the substantially continuous and coplanar conical surface as shown in FIG. 3, presenting approximately equal length segments of the distal end 44 of the mandrel 32 and the truncated conical segment 50 of the ventilation tube 12 measured along the longitudinal axes thereof.

Referring particularly to FIGS. 4–7, it may be seen that a helical channel, groove, or thread 54 is then cut, etched, or otherwise formed into the substantially continuous and coplanar conical surface defined by the distal end 44 of the mandrel 32 and the truncated conical segment 50 of the ventilation tube 12. One suitable method for forming the helical thread 54 into the mandrel 32 and ventilation tube 12 consists of using an orbiting electrode configuration electrical discharge machining (EDM) process well known to the art of machining precision medical devices.

In the ventilation tube 12 described above, the helical thread 54 extends approximately 3½ turns about the entire length of the substantially continuous and coplanar conical surface, with approximately 1¾ turns of the helical thread being disposed on each of the distal end 44 of the mandrel 32 and the truncated conical segment 50 of the ventilation tube 12. The helical thread 54 is approximately 0.5 mm in width with lands between each groove of approximately 0.2 mm width, with both the forward and rear faces 56, 58, respectively, of each turn of the helical thread 54 being generally planar and radially perpendicular with the corresponding longitudinal axes of the mandrel 32 and ventilation tube 12. The depth of the helical thread 54 may be approximately equal to the width of the lands, or may alternately be variable throughout different sections of the distal end 44 of the mandrel 32 and the truncated conical segment 50 of the ventilation tube 12 to provide a progressive increase in the diameter of the core 60 of the helical thread 54 until a maximum diameter of the core 60 approximately equal to the outer radial surface of the seating region 26 of the ventilation tube 12 is achieved. The helical thread 54 therefore has a relatively constant pitch which is defined by the number of rotations or revolutions of the helical thread 54 between the distal tip 44 of the fixture and the trailing edge of the helical thread 54 at the rear surface of the front flange 18 divided by the longitudinal length thereof. The pitch of the helical thread 54 and its rate of rotation about the longitudinal axis will determine the linear rate at which the ventilation tube 12 is drawn through the membrane 28. A non-uniform or non-constant pitch may also be utilized in some applications where the progression of the ventilation tube 12 through the membrane 28 is not linearly constant, such as accelerating or decelerating as progression continues.

Referring particularly to FIGS. 2–7, it may be seen that the assembled fixture 30 and the ventilation tube 12 are fixedly mounted to a rigid or flexible shaft 62 that is surrounded or circumscribed by a rigid or flexible sheath or sleeve 64 extending substantially along the length of the shaft 62. In the embodiment shown in FIG. 2–7, a flexible or resilient shaft 62 such as a wrapped metal coil or spiral strip is shown. Alternately, a limited segment of the shaft 62 disposed adjacent to the ventilation tube 12 may be flexible or resilient, or the shaft 62 and fixture 30 may be formed integrally from a substantially rigid or inflexible material as described below.

The proximal end 66 of the shaft 62 is operatively connected to a rotational drive assembly 68 capable of selectively imparting rotational motion and torque to the shaft 62, with the shaft 62 rotating within the sleeve 64 to in turn rotate the fixture 30 and the ventilation tube 12. Consequently, the distal end 70 of the sleeve 64 is initially displaced a small distance on the order of 0.001" from the rear face 24 of the ventilation tube 12 to prevent frictional engagement or contact between the ventilation tube 12 and sleeve 64, which may be achieved by inserting a thin paper or tissue washer on the shaft 62 between the distal end 70 of the sleeve 64 and rear face 24 of the ventilation tube 12 when the ventilation tube 12 is mounted on the fixture 30.

Figure 1:
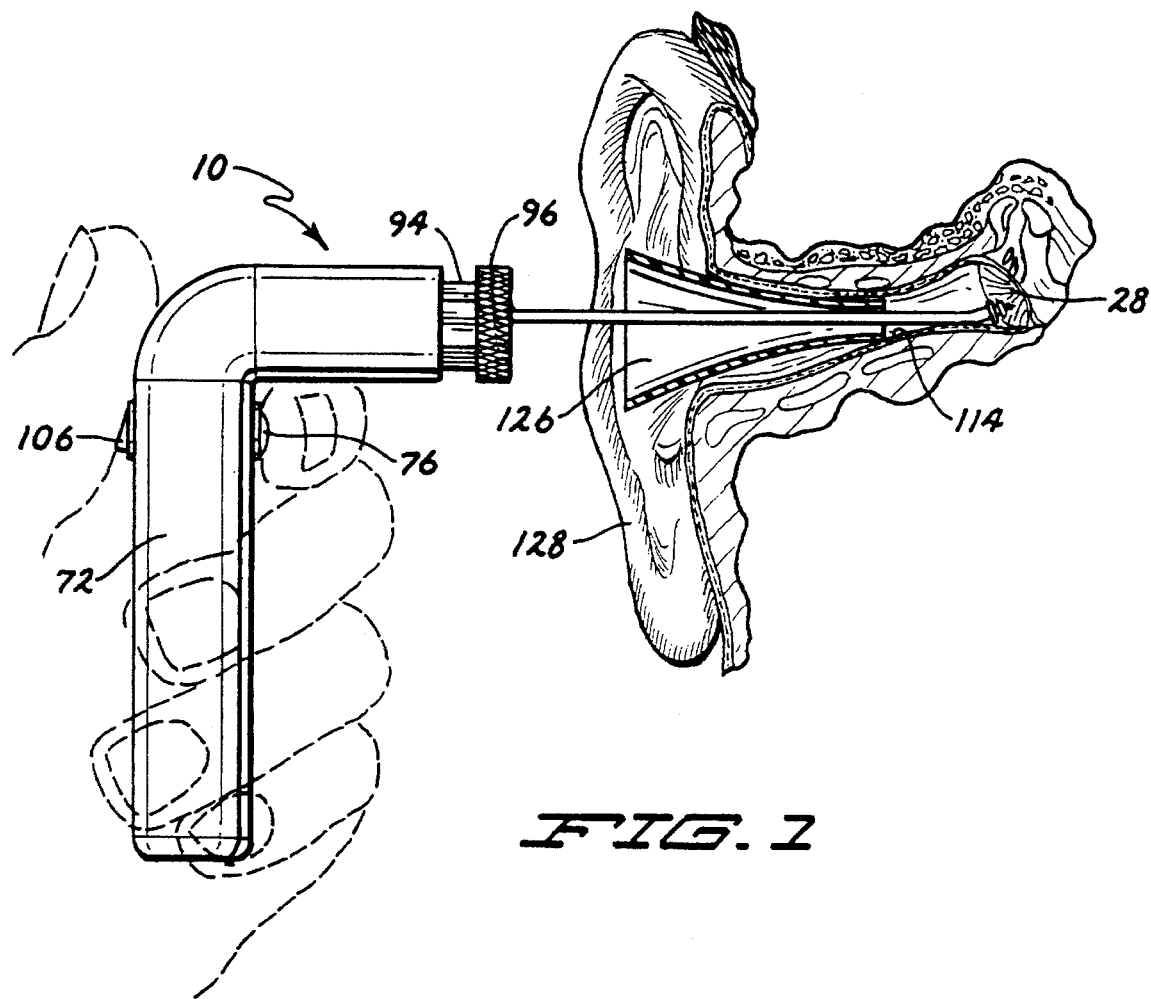
FIG. 1 is partially broken away cross section view of a human ear showing the hand-held embodiment of the apparatus for implanting a medical ventilation tube of this invention.
Figure 5:
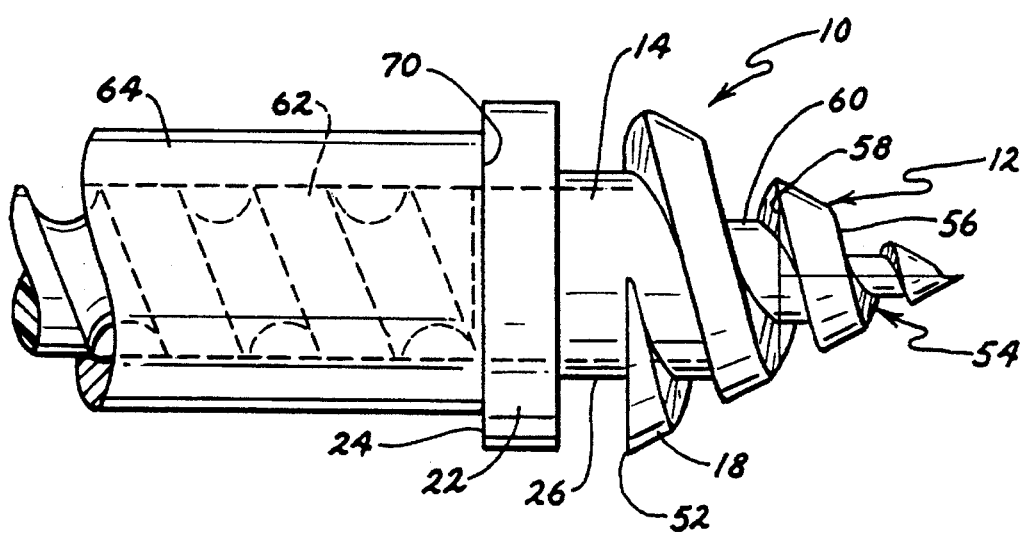
FIG. 5 is a side elevation view of the mandrel and ventilation tube of FIG. 3 showing the sleeve surrounding the shaft.
Figure 6:
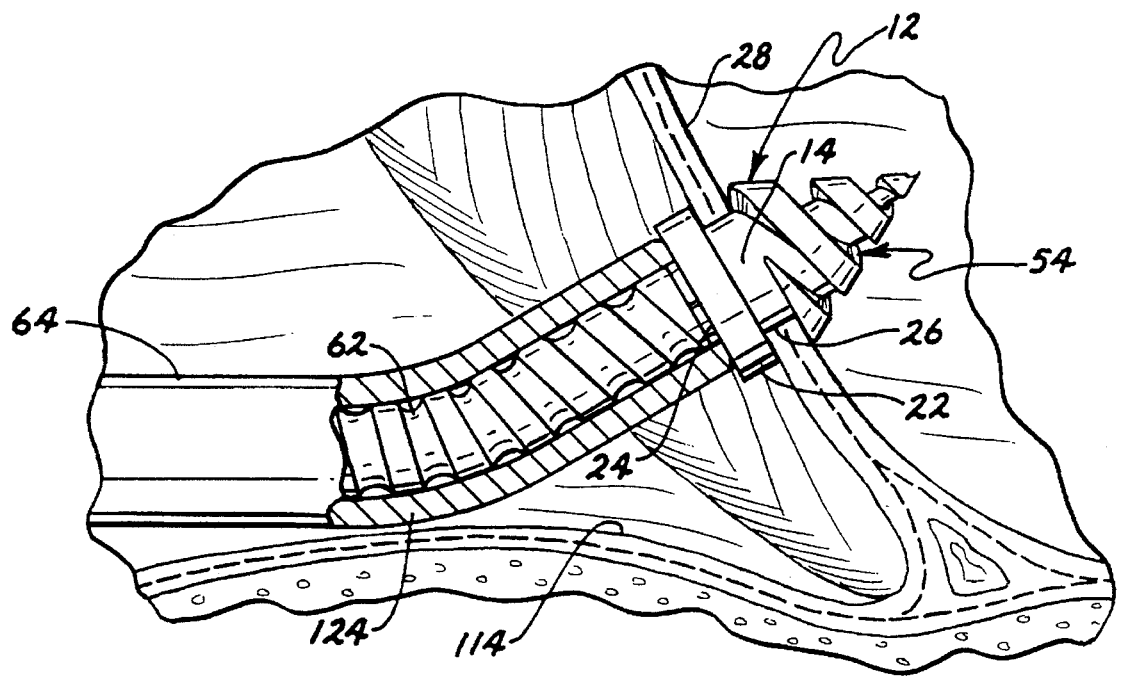
FIG. 6 is a side elevation view of the mandrel and ventilation tube of FIG. 4 showing the ventilation tube completely received or implanted through the membrane, and further showing an embodiment of the mandrel or shaft which provides a bend adapted to maintain the axis of rotation of the mandrel perpendicular to the normal plane of the membrane during insertion and retraction.
Figure 7:
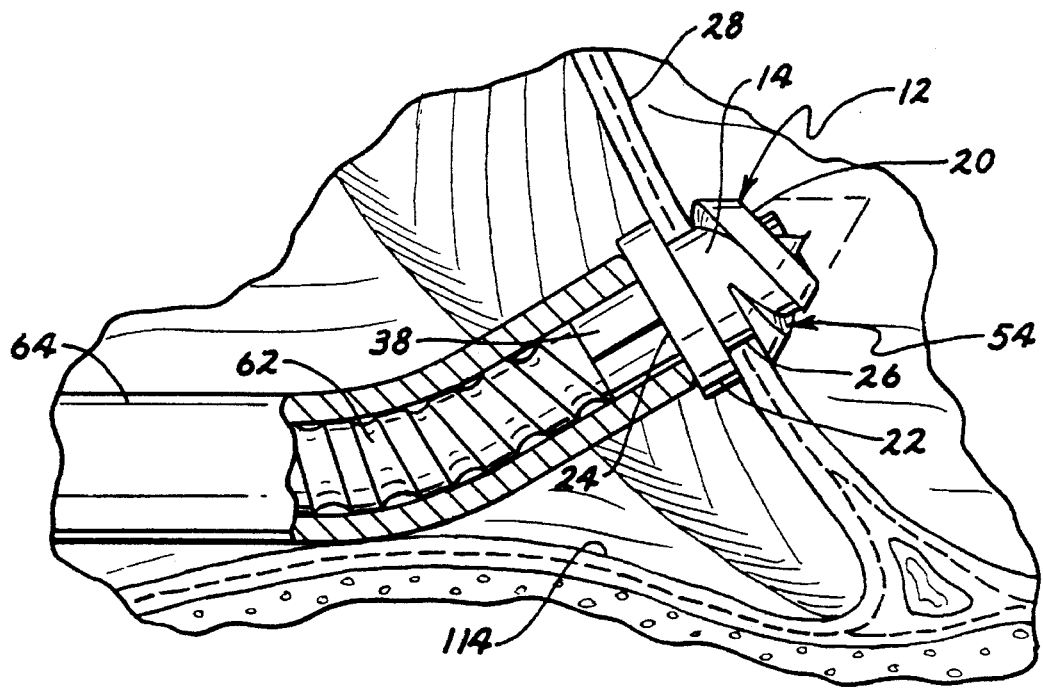
FIG. 7 is a side elevation view of the mandrel and ventilation tube of FIG. 5 showing the mandrel partially retracted from the ventilation tube through the bore thereof.

Referring to FIGS. 1, 6, and 7, the tip of the distal end 44 of the mandrel 32 comprising the lead penetrating edge of the helical thread 54 may be placed in direct contact with the substantially intact membrane 28 at a desired position or location within a defined region, with the tip of the distal end 44 of the mandrel 32 and lead penetrating edge of the helical thread 54 being pressed lightly against the membrane 28 as the rotational drive assembly 68 rotates the shaft 62, fixture 30, and ventilation tube 12 in order to cause the penetrating edge of the helical thread 54 to penetrate the membrane 28 and draw the mandrel 32 and forward flange 18 of the ventilation tube 12 through the membrane 28 at a controlled rate until the membrane 28 is disposed within the generally cylindrical seating region 26 of the body 14 between the forward flange 18 and rear flange 22 as shown in FIGS. 6 and 7. Tension may be placed on the fixture 30 and ventilation tube 12 to pull or retract the portion of the membrane 28 adjacent to the implantation location axially outward from its normal plane and from any delicate structures located on the opposing side of the membrane 28. It may be appreciated that while the initial portion of the passage will be formed by the penetrating edge of the helical thread, and that penetrating edge may extend along the length of the helical thread 54, the shape and size of the eventual passage that is formed is produced by the core 60 of the helical thread 50 actually stretching the fibers of the membrane 28 as the ventilation tube 12 progresses linearly through the membrane 28. Because the position of the ventilation tube 12 relative to the plane of the membrane 28 is limited to the area between the confronting front and rear faces 56, 58 of the helical thread 54, the rate of penetration or linear progression of the ventilation tube 12 through the membrane 28 is directly proportional to and may be precisely controlled by the rate of angular revolution (RPMs) of the ventilation tube 12 about its axis of rotation.

Rotation of the shaft 62, fixture 30, and ventilation tube 12 is then discontinued, and the mandrel 32 is withdrawn or retracted axially from within the bore 16 of the ventilation tube 12 by withdrawing or retracting the shaft 62 into the sleeve 64, with the distal end 70 of the sleeve 64 contacting the rear face 24 of the ventilation tube 12 to prevent the ventilation tube 20 from moving rearwardly along with the mandrel 32, fixture 30, and shaft 62 as shown in FIG. 7.

Referring again to FIGS. 1 and 8, a hand-held embodiment of the apparatus 10 of this invention including the rotational drive assembly 68 is shown. The rotational drive assembly 68 is disposed within a housing 72 and includes a drive motor 74 which may be any type of motor such as pneumatically driven by a remote supply of compressed or pressurized gas, or a DC motor powered by an AC electrical adapter and transformer or rechargeable battery. Pneumatic motors or drives are preferred in medical settings due to the availability of standardized supply lines for compressed or pressurized gasses at specific and variably regulated pressures, and the diminished potential for electrical shocks or sparks in environments in which oxygen and combustible anesthetics may be used. In the event an electrical drive motor is desired, a DC motor and gear train to reduce the resultant RPMs and increase torque are preferred, with an integral braking clutch which engages when power is interrupted providing precise control over angular velocity.

The drive motor 74 of the rotational drive assembly 68 is actuated by depressing a trigger or switch 76 on a portion of the housing 72 easily gripped by the user, which causes the motor shaft 78 to rotate a first gear 80 at a predetermined or variable angular rate. The first gear 80 contacts and meshes with a second gear 82 thereby forming a right-angle differential. The second gear 82 is connected by an intermediate spindle 84 to a socket 86 defining a hexagonal cross-section recess 88 into which an elongated slide member 90 is partially but engagingly received. The slide member 90 may slide axially within the recess 88, however rotation of the socket 86 is transmitted uniformly to the slide member 90 without vibration or slippage. A generally cylindrical guide segment 92 having a threaded tip extends from the front end of the slide member 90, the guide segment 92 and slide member 90 being retained within the housing by an annular collar 94 and retaining ring 96 which engages the front end of the housing 72.

The proximal end 98 of the sleeve 64 and proximal end 66 of the shaft 62 within the sleeve 64 are received through an aperture 100 in the retaining ring 96 and between the tapered clamping fingers 102 of the chuck 104 projecting from the annular collar 94. The proximal end 66 of the shaft 62 is engagingly received and secured within a matingly threaded bore in the front end of the guide segment 92, while the proximal end 98 of the sleeve 64 is clamped in position relative to the annular collar 94 and shaft 62. Assembly is completed by screwing the threaded tip of the cylindrical guide segment 92 of the slide assembly 90 completely into the interior of annular collar 94, preferably through approximately three revolutions, until the tip of the slide assembly 90 can move freely within the interior of the annular collar 94 restrained from unintentional removal by the threads. The threaded proximal end 66 of the shaft 62 is screwed tightly into mating threads within the slide assembly 90 so that the shaft 62 moves axially or longitudinally with the slide assembly 90, and the proximal end 98 of the sheath 64 is clamped and held in a fixed position relative to the annular collar 94 by inward radially pressure exerted by the retaining ring 96 being screwed tightly onto the tapered clamping fingers 102 to compress those fingers 102 into engaging contact with the sleeve 64.

In most applications, it is envisioned that the ventilation tube 12 will be mounted on the fixture 30 which is integrally formed with or fixedly attached to the shaft 62 and received within the sleeve 64. The disposable elements will be enclosed in a sterile tamper-evidencing package (not shown) for removal in the surgical environment. The disposable elements will be removed from their sterile enclosure immediately prior to the implantation, and securely mounted to the rotational drive assembly 68 as described above. Referring to FIG. 8, it is anticipated that the disposable elements will include the slide assembly 90, annular collar 94, retaining ring 96, sleeve 64, shaft 62, fixture 30, and the vent tube 12.

Once the ventilation tube 12 has been successfully positioned and at least partially or completely inserted through the membrane 28, the fixture 30 is disengaged from the ventilation tube 12 by withdrawing the mandrel 32 from within the bore 16. This withdrawal is accomplished by manually depressing the retraction mechanism 106 which is pivotally mounted such that pressure on the retraction mechanism 106 withdraws a catch lever 108 having a prong 110 engaging the front edge 112 of the slide member 90 to retract the slide member 90 rearwardly into the recess 88 of the socket 86. Retracting the slide member 90 causes the shaft 62 to move rearwardly within and relative to the sleeve 64, with pressure from the distal end 70 of the sleeve 64 preventing rearward movement of the ventilation tube 12, thus disengaging the ventilation tube 12 from the mandrel 32 and retracting the mandrel 32 and fixture 30 further into the sleeve 64. For ventilation tubes 12 of the type discussed above, a rearward linear or axial movement of only 4 mm is required to completely withdraw the fixture 30 from within the ventilation tube 12.

After the ventilation tube 12 is implanted, the distal end 70 of the sleeve 64 is removed from the patient's ear canal or other passageway 114 surrounding the membrane 28. The slide member 90 is either manually drawn or may be spring biased forward when the retraction handle 106 is released by a compression-type spring 118 located at the rear of the recess 88 in the socket 86 and contacting the base end of the slide member 90. The disposable elements are discarded and replaced with new sterile disposable elements, thus placing the apparatus 10 in condition for another implantation.

As an alternate retraction mechanism, a pivoting retraction handle (not shown) may be disposed vertically in front of the slide assembly 90 with the top end pivotally connected to the housing 72 and having a free lower end extending through an opening in the bottom of the housing 72 proximate to the region normally gripped by the user. The retraction handle defines a keyway having a narrowed upper section and an enlarged lower section, the lower section being capable of receiving the proximal ends 98, 66 of the sleeve 64 and shaft 62 therethrough, with the narrowed upper section being sized so as to receive the sleeve 64 freely therethrough as the retraction handle pivots rearwardly to contact the front edge 112 of the slide member 90, and retracting the slide member 90 rearwardly into the recess 88 of the socket 86 as the retraction handle continues to be pivoted rearwardly. Again, the retraction may be opposed by a spring bias such as the compression-type spring 118 disposed within the recess 88 of the socket 86 and contacting the base end of the slide member 90. Any pivoting retraction handle should be disposed sufficiently forward from the gripping region of the housing 72 so that the retraction handle is not inadvertently or prematurely retracted as the physician reaches for or operates the switch 76.

Figure 10:
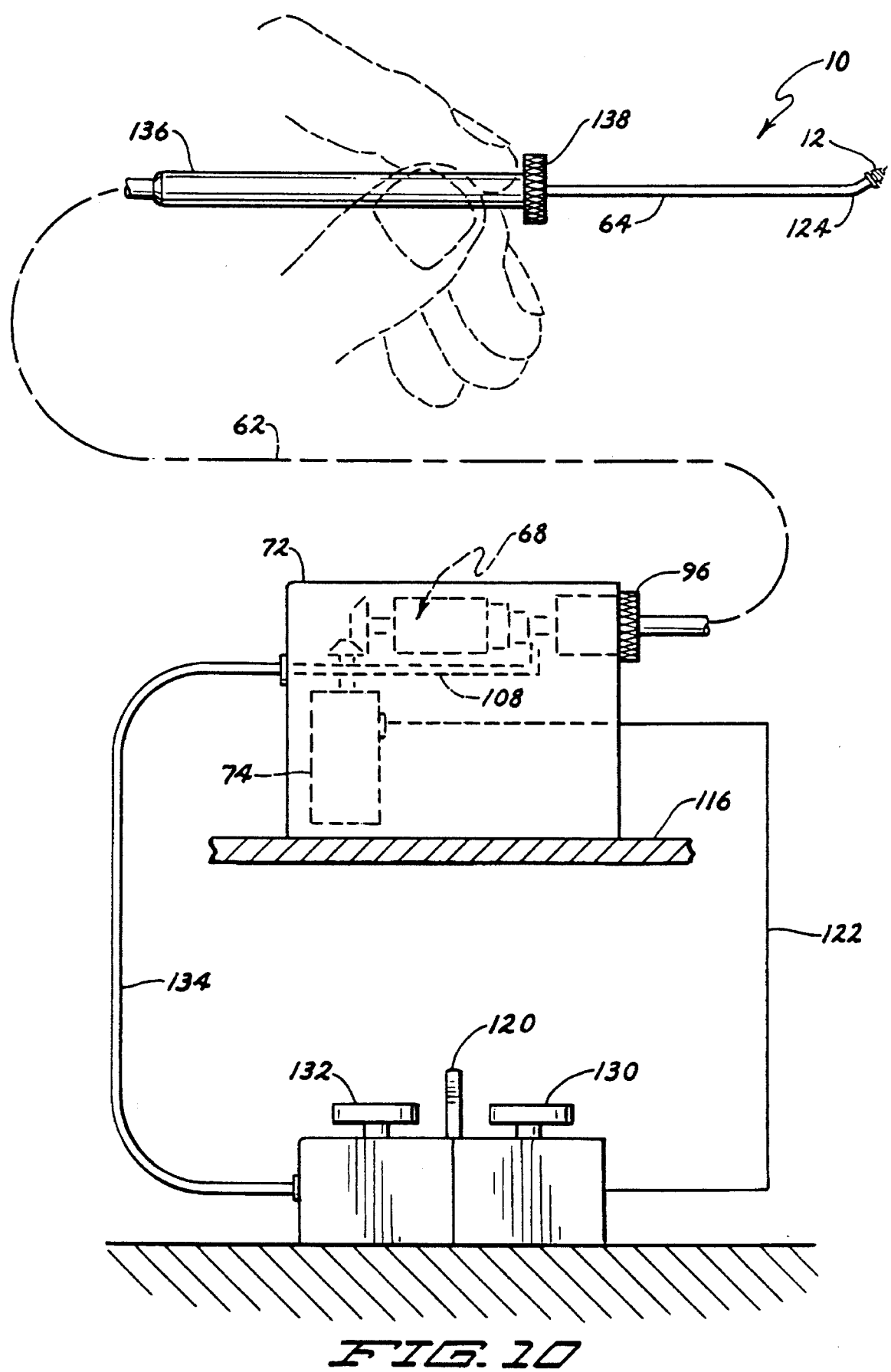
FIG. 10 is a diagrammatic view of the installed embodiment of the instrument used to implant ventilation tubes according to the method and apparatus of this invention.

Referring to FIG. 10, an installed embodiment of the apparatus 10 including the rotational drive assembly 68 is shown for installation in a dedicated location such as a surgical room. The drive motor 74 is housed within a housing 72 that may be mounted to a support 116 such as a surgical table, stand, tray, wall, or floor. In such a configuration, the drive motor 74 will include a power connection such as a quick-connect valve for pressurized gas if the drive motor 74 is pneumatic, or a grounded and sheathed electrical cord if the drive motor 74 is electric. In the event an electric motor is used, the power connection may include an AC to DC converter located within the housing 72 or at a remote location proximate to the main power supply.

A control connection 122 extends from the housing 72 and is operatively connected to the drive motor 74. The control connection 122 is linked to a drive actuator 130, such as a pressure-activated foot pedal placed on the floor near the operator or a pressure-activated trigger mechanism clamped or attached to a handgrip 136 surrounding the shaft 62 and sleeve 64 in the region that would normally be gripped by the operator performing the implantation. The control connection 122 preferably permits variable speed control and high sensitivity and accuracy over starting and stopping the rotation of the drive motor 74, and provides a switching mechanism that is operatively connected directly to the drive motor 74 or to a solenoid valve if the drive motor 74 is pneumatic.

A retraction actuator 132 such as a pressure-activated foot pedal is operatively connected by a cable release 134 or similar assembly to the catch lever 108 within the housing 72, such that depressing the retraction actuator 132 retracts the catch lever 108 and draws an intermediate section of the cable or shaft 62 within an intermediate section of the sleeve 64. In situations where a foot pedal is utilized for both the drive actuator 130 and retraction actuator 132, a barrier 120 between the two should be provided to prevent accidental or premature retraction of the shaft 62 within the sleeve 64.

In such an embodiment, it is anticipated that the length of the intermediate shaft 62 and sleeve 64 may be increased significantly compared to the hand-held instrument embodiment, and may extend to a length of several feet to permit maximum range of motion and ease of use for the operator. In such an event, the majority of the shaft 62 and sleeve 64 will preferably be of a relatively flexible construction, such as a wrapped cable or spring shaft 62 and a Teflon® or polymer sleeve 64. The diameter of this intermediate shaft 62 and sleeve 64 may be increased significantly in the region disposed between the housing 72 and handgrip 136, with the handgrip 136 providing an interior cavity and coupling assembly for a disposable shaft 62 and sleeve 64 similar to the coupling assembly described above in relation to the hand-held embodiment. In such a case, the distal end of the shaft 62 would be screwed into a threaded bore in the slide assembly 90 slidably mounted within the handgrip 136 and permanently connected to the intermediate cable or shaft 62, with the sleeve 64 then being clamped between the tapered clamping fingers 102 of the chuck 104 that is fixedly mounted at the forward end of the handgrip 136 by inward radially pressure exerted by the retaining ring 138 being screwed tightly onto the tapered clamping fingers 102 to compress those fingers 102 into engaging contact with the sleeve 64.

In applications in which the shaft 62 is flexible, a portion of the sleeve 64 adjacent to the distal end 70 thereof may be substantially more rigid and form a predetermined or adjustable angle or bend 124, thus causing the shaft 62 to flex within the sleeve 64. The bend may be positioned and oriented at such an angle or attitude to permit the axis of rotation of the ventilation tube 12 and distal tip 44 of the mandrel 30 to be as perpendicular to the normal plane of the membrane 28 as possible during implantation.

In operation, the patient into whose tympanic membrane 28 the ventilation tube 12 will be implanted is positioned as appropriate on a surgical platform, and is either anesthetized to prevent movement or given a local anaesthetic. It is anticipated that the speed and increased accuracy provided by the method and apparatus of this invention will reduce the need for general anesthetics in adults, and minimization of any discomfort caused by axial pressure to the tympanic membrane 28 that is not blocked by a local anaesthetic. An appropriate speculum 126 is inserted through the outer ear 128 of the patient and into the ear canal or passage 114.

A sterile package is provided containing one or more sets of the disposable elements including a ventilation tube 12 mounted on the fixture 30 with a shaft 62, sleeve 64, and the mating coupling such as the threaded proximal end 66 required for an operative connection to the rotational drive assembly 68. The package is opened, and the contents are removed and operatively connected to the rotational drive assembly 68. The physician grips an appropriate and comfortable portion of the housing 72 in the hand-held embodiment, or the handgrip 136 in the installed embodiment, and places the tip 44 of the mandrel 32 through the speculum 126 and passage 114 and into contact with a substantially intact region of the membrane 28 of the patient at the desired location, usually in the lower anterior quadrant thereof.

The physician then selectively engages the rotational drive assembly 68 by activating the drive actuator 130 or 76, which initiates rotation of the shaft 62, fixture 30, and ventilation tube 12 at a predetermined or controllable angular rate. It may be appreciated that in some applications, the physician may manually rotate the shaft 62 and sleeve 64, in which case the physician's hand and device used for holding the shaft 62 and sleeve 64 would be considered the rotational drive.

The helical thread 54 at the tip 44 of the mandrel 32 penetrates the membrane 28 creating a passage, and the helical thread 54 will continue to be drawn through the membrane 28 at a controlled rate thereby enlarging the passage by stretching the fibers of the membrane 28 until the ventilation tube 12 is at least partially implanted through the membrane 28. The rotation and implantation is continued until the entire front section 18 of the ventilation tube 12 has passed through the passage in the membrane 28, and the membrane 28 is disposed within the seating region 26. Linear advancement or progression of the ventilation tube 12 through the membrane 28 is automatically arrested when the membrane 28 passes into the seating region 26 beyond the rear face of the forward flange 18 and trailing end of the helical thread 54, and by contact between the membrane 28 and the rear flange 22, although rotation of the ventilation tube 12 may still be continued through several rotations without damaging the membrane 28.

The physician then deactivates the rotational drive assembly 68 to terminate rotation of the shaft 62, fixture 30, and ventilation tube 12, and manually depresses the retraction mechanism 106 or the retraction actuator 132 to withdraw the mandrel 32 from within the bore 16 of the ventilation tube 12 or otherwise disengage and detach the ventilation tube 12 from the fixture 30, with the ventilation tube 12 remaining implanted through the membrane 28.

Various other manners for practicing either the method or apparatus of this invention are contemplated as being suitable for various applications, as may be readily appreciated by those skilled in the art.

For example, the ventilation tube 12 may initially be mounted on the mandrel 32 and held in place by a circular cross section O-ring which circumscribes the mandrel 32 and is partially received within a recess or groove encircling the mandrel 32, thus retaining the separate sections 34, 36 of the mandrel 32 together and providing frictional engagement with the inner surface of the bore 16 of the ventilation tube 12. This process may be desired in the event that multiple implantations are to be performed, and the fixture 30, shaft 62, and sleeve 64 are not disposed of or replaced for each implantation, but rather one or more additional ventilation tubes 12 are manually mounted on the fixture 30 or by using a rapid automated mounting apparatus that dispenses and mounts a ventilation tube 12 onto the fixture 30.

Alternately, particularly in cases where the ventilation tube is fabricated from a more resilient rather than rigid material, one or more splines or projections extending radially from the mandrel 32, or projecting forwardly from the distal end 70 of the sleeve 64 or rearwardly from the rear face 24 of the ventilation tube 12, may engage a corresponding adjacent surface and prevent axial movement or rotation of the ventilation tube 12 relative to the fixture 30 or sleeve 64. It is anticipated that in some applications it will be unnecessary to prevent or limit rotation of the ventilation tube 12 relative to the fixture 30, since the helical thread 54 will normally be self-aligning or self-compensating as the leading edge of the rotating helical thread 54 of the ventilation tube 12 contacts the membrane 28.

Similarly, particularly in cases of molded ventilation tubes 12, the mandrel 32 and bore 16 may have a square or other non-circular or non-uniform cross-section which engage one another and effectively prevent rotation or axial slippage, but which permit retraction of the mandrel 32 from the bore 16 in the same manner as described above.

The helical thread 54 may be molded into one or both of the ventilation tube 12 or fixture 30 when fabricated from a resinous, moldable, or thermoformable material, or may be cut or etched using any procedure appropriate to the particular materials from which the fixture 30 and ventilation tube 12 are fabricated. The helical thread 54 may also be shaped and formed with non-parallel lands, or an increasingly deeper groove (traversing from the distal to proximal end thereof), so as to increase the capability for using the helical thread 54 to pull or retract the membrane 28 axially away from any physiological structures disposed on the opposite side of the membrane 28. (In such a case it might appear that the membrane 28 is actually drawn partially over the helical thread 54 of the ventilation tube 12, but for purposes of this application it shall be considered that the ventilation tube 12 is also drawn through the membrane 28.)

The fixture 30 need not include a mandrel 32, but may comprise any suitable clamp or attachment device having at least one surface which grips or engages the ventilation tube 12 either along the rear face 24 or any exterior surface of the body 14 behind the front face 20, and which does not obstruct the helical thread 54 while maintaining the ventilation tube 12 in a predetermined position or orientation relative to that fixture 30.

The term "substantially intact membrane 28" as used herein refers to a membrane 28 that does not have an initial incision in the region in which the ventilation tube 12 is to be implanted that is sufficient in size to receive the ventilation tube 12 therethrough without enlarging or stretching that incision opening, but does include a membrane 28 which has been pierced, punctured, or lanced using a hypodermic syringe needle, probe, or myringotomy instrument for the purpose of withdrawing fluid, equalizing pressure, permitting visual inspection using a myringotomy scope or fiber optic instrument, or aligning or pre-positioning the exact location for the ventilation tube 12 within the optimal region of the membrane 28 at which the ventilation tube 12 is to be implanted.

Referring particularly to FIG. 9, a preferred method of fabricating the fixture 30 unitarily with the shaft 62 and for subsequently machining the helical thread 54 into the fixture 30 and ventilation tube 12 is shown in which the shaft 62 comprises a generally cylindrical rod of titanium having an overall length of approximately 6" and a maximum diameter of 0.050". The rod defines a 4" straight segment 140 having a constant radius $R_1$ of 0.025", and a 2" tapered segment 142 which tapers from radius $R_1$ of 0.0250" at junction 144 to a final radius $R_2$ of approximately 0.0225". The ventilation tube 12 is fabricated from titanium or a compatible metal with a straight bore 16 having a uniform diameter of 0.048", and is mounted onto the tapered segment 142 using a controlled press fit by applying from about 1–10 lbs. of axial pressure until the ventilation tube 12 is disposed approximately at the midpoint of the tapered segment 142. The tapered segment 142 is then blunt-sheared at a cut point 146 corresponding to the distal tip 44 of the fixture 30, and the remainder of the tapered segment 142 adjacent the forward flange 18 of the ventilation tube 12 is ground or machined to form a conical surface 148 that is substantially continuous with the truncated conical surface of the forward flange 18 of the ventilation tube 12. The helical thread 54 is then machined using an EDM process as described above. In operation, retraction of the shaft 62 from within the ventilation tube 12 a distance of approximately 0.1 mm will disengage the shaft 62 from the ventilation tube 12, with continued retraction of up to 4 mm completely withdrawing the fixture 30 from within the ventilation tube 12.

It is anticipated that various other types of ventilation tubes 12 may be utilized with the method and apparatus 10 of this invention, including but not limited to those shown or described in the references submitted with this application, such as: collar button or bobbin type ventilation tubes (including Sheehy, Reuter, or Treace designs) having generally cylindrical or elliptical central body regions surrounding the bore or lumen; Baxter ventilation tubes having a flared conical rear flange: pediatric ventilation tubes in which the forward flange has a greater diameter than the rear flange; spoon bobbin ventilation tubes in which the forward flange has a radial eccentricity or angled radial tab (including Armstrong grommets, Shah, Richards, Shea, and ETV ventilation tubes); Shepard grommets, Sultan ventilation tubes, and Berger "V" bobbins in which the body defines a concave or V-grooved surface extending completely between the forward flange and rear flange; Rock pediatric ventilation tubes in which the inner face of one flange is beveled; Paparella ventilation tubes in which the forward flange defines a notch and the rear flange defines an axially extending tab (and corresponding variations such as the Chop ventilation tube); Donaldson bobbins; T-, butterfly, and split ventilation tubes (including variations such as Baxter, Cohen, Rube, Redfield, Siegel, Duberstein, Richards, and JSK); arrow ventilation tubes (including variations such as Gross and Linderman-Silverstein ventilation tubes); straight ventilation tubes having a single flange (including Armstrong plain end, Improved Armstrong, Per-Lee angled rear flange, and Jahn HydroxylVent ventilation tubes); Feuerstein ventilation tubes; Pappas tri-flange ventilation tubes; DiBartolomeo obturated ventilation tubes; mesh ventilation tubes; Silverstein malleus clips; as well as Armstrong beveled grommets and Pope ventilation tubes having one or both flanges angled radially relative to the body.

While the preferred embodiments of the above method and apparatus 10 have been described in detail with reference to the attached drawing Figures, it is understood that various changes and adaptations may be made in the method and apparatus 10 without departing from the spirit and scope of the appended claims.

What is claimed is:

1. A method for implanting a ventilation tube through a substantially intact region of a membrane of a person at a desired location, said ventilation tube having a body defining a bore, a front section, and a rear section, said membrane having a normal plane, said method comprising the steps of:

providing a fixture which engages at least one surface of the body of the ventilation tube to generally maintain the ventilation tube in a predetermined position relative to said fixture;

providing a portion of said fixture or the front section of the ventilation tube with a penetrating edge, said penetrating edge being disposed such that rotation of said penetrating edge about an axis of rotation generally perpendicular to the normal plane of the membrane and generally parallel with the bore of the ventilation tube will cause said penetrating edge to penetrate through the substantially intact region of the membrane;

providing a portion of said fixture and the front section of the ventilation tube with a threaded portion, said threaded portion extending at least partially between said fixture and the front section of the ventilation tube;

placing a portion of said penetrating edge in contact with the membrane of the person at the desired location within the substantially intact region;

rotating said penetrating edge and said threaded portion such that said penetrating edge penetrates the membrane, and said portion of the fixture and the front section of the ventilation tube defining said threaded portion is drawn through the membrane, so that the ventilation tube is at least partially implanted through the membrane; and detaching said fixture from the ventilation tube such that the ventilation tube remains at least partially implanted through the membrane of the person at the desired location, whereby the ventilation tube is at least partially implanted through the membrane of the user.

2. The method of claim 1 wherein the fixture is a mandrel, said mandrel having a distal end, the front section of the ventilation tube having a front face, said mandrel being received at least partially within the bore of the ventilation tube and extending axially outward beyond said front face of the front section.

3. The method of claim 2 wherein the distal end of the mandrel defines the portion of the penetrating edge which contacts the membrane.

4. The method of claim 3 wherein both the distal end of the mandrel and the front section of the ventilation tube define the threaded portion.

5. The method of claim 2 wherein the ventilation tube does not rotate relative to the mandrel.

6. The method of claim 2 wherein the bore of the ventilation tube has an inner surface and the mandrel defines an outer surface contacting the ventilation tube, and wherein the ventilation tube is prevented from rotating substantially relative to the mandrel by frictional engagement between said inner surface of the ventilation tube and said outer surface of the mandrel which contacts the ventilation tube.

7. The method of claim 2 wherein the step of detaching the fixture from the ventilation tube comprises:

withdrawing the mandrel axially from within the bore of the ventilation tube while exerting pressure against the ventilation tube in a direction towards the membrane.

8. The method of claim 1 wherein the threaded portion is generally helical and is defined by and extends between both the fixture and the front section of the ventilation tube.

9. The method of claim 1 wherein the ventilation tube is prevented from rotating or axially sliding relative to the fixture by frictional engagement between the ventilation tube and the fixture.

10. The method of claim 1 wherein prior to the step of detaching the fixture from the ventilation tube the method further comprises the step of:

exerting tension on the threaded portion in a direction generally away from the normal plane of the membrane such that the threaded portion pulls at least an adjacent portion of the membrane out of the normal plane.

11. The method of claim 1 wherein the threaded portion has a pitch and the ventilation tube is rotated at a rate of rotation, and wherein the ventilation tube is drawn through the membrane at a controlled rate of linear progress determined by said pitch of the threaded portion and said rate of rotation.

12. The method of claim 1 wherein the ventilation tube has a seating region and the threaded portion has a trailing end generally proximate to said seating region, and wherein the ventilation tube is drawn through the membrane at a controlled rate of linear progress until the membrane passes beyond said trailing end of the threaded portion and is generally disposed within said seating region.

13. The method of claim 1 wherein the ventilation tube may continue to be rotated after the ventilation tube is drawn through the membrane and the membrane is generally disposed within said seating region, without the continued rotation moving the ventilation tube substantially linearly relative to membrane or damaging the membrane.

14. In a combination of a ventilation tube and an improvement for implanting said ventilation tube through a substantially intact region of a membrane of a person at a desired location, said ventilation tube having a body defining a bore, a front section, and a rear section, the improvement comprising:

a fixture, said fixture engaging at least one surface of the body of the ventilation tube to maintain the ventilation tube in a predetermined position relative to said fixture, said fixture or the front section of the ventilation tube or both having a penetrating edge, at least a portion of said fixture and the front section of the ventilation tube having a threaded portion extending therebetween, said fixture and said threaded portion having an axis of rotation oriented generally parallel with the bore of the ventilation tube; the penetrating edge being placed contact with the substantially intact region of the membrane and rotated about the axis of rotation, the penetrating edge being disposed such that rotation of the penetrating edge about the axis of rotation will cause the penetrating edge to penetrate through the substantially intact region of the membrane, and the portion of the fixture or the front section of the ventilation tube defining the threaded portion being drawn at least partially through the membrane until the ventilation tube is at least partially implanted through the membrane.

15. The improvement of claim 14 wherein the front section of the ventilation tube has a front face and the fixture further comprises:

a mandrel, said mandrel having a distal end, said mandrel being received at least partially within the bore of the ventilation tube and extending axially outward beyond the front face of the front section.

16. The improvement of claim 15 wherein the distal end of the mandrel defines at least a portion of the penetrating edge which contacts the membrane.

17. The improvement of claim 16 wherein both the distal end of the mandrel and the front section of the ventilation tube define the threaded portion.

18. The improvement of claim 15 wherein the ventilation tube does not rotate relative to the mandrel.

19. The improvement of claim 15 wherein the bore of the ventilation tube has an inner surface and the mandrel defines an outer surface contacting the ventilation tube, and wherein the ventilation tube is prevented from rotating substantially relative to the mandrel by frictional engagement between said inner surface of the ventilation tube and said outer surface of the mandrel which contacts the ventilation tube.

20. The improvement of claim 15 wherein the mandrel may be axially withdrawn from within the bore of the ventilation tube to selectively detach the ventilation tube from the mandrel.

21. The improvement of claim 20 further comprising:

a shaft, said shaft being connected to the mandrel; and a sleeve, said sleeve generally circumscribing and at least partially enclosing said shaft.

22. The improvement of claim 21 wherein at least a portion of the sleeve contacts the ventilation tube when the mandrel is axially withdrawn from within the bore of the ventilation tube, the sleeve preventing the ventilation tube from moving axially relative to the sleeve as the mandrel is withdrawn from within the bore of the ventilation tube.

23. The improvement of claim 22 wherein the shaft and the fixture are fabricated from a rod, said rod having a pair of ends and a tapered segment proximate to one of said pair of ends, said ventilation tube initially being mounted on said tapered segment by a pressure fit with said tapered segment being received through the bore of the ventilation tube.

24. The improvement of claim 23 wherein the front section of the ventilation tube has a truncated conical shape, and wherein a portion of the tapered segment of the rod is ground to form a conical shape, such that said conical shape of the tapered segment of the rod and said truncated conical shape of the front section of the ventilation tube define a substantially continuous conical surface.

25. The improvement of claim 21 wherein the fixture is fabricated unitarily with the shaft.

26. The improvement of claim 14 wherein the threaded portion is generally helical and is defined by and extends between both the fixture and the front section of the ventilation tube.

27. The improvement of claim 14 wherein the ventilation tube is prevented from rotating or axially sliding relative to the fixture by frictional engagement between the ventilation tube and the fixture.

28. The improvement of claim 14 wherein the ventilation robe is fabricated from a metal.

29. The improvement of claim 28 wherein at least a portion of the fixture is fabricated from the metal from which the ventilation tube is fabricated.

30. The improvement of claim 14 further comprising: a rotational drive, said rotational drive being operatively connected to the fixture for selectively rotating the fixture about the axis of rotation.

* * * * *